United States Patent [19]

Mendelsohn

[11] Patent Number: 4,846,828
[45] Date of Patent: Jul. 11, 1989

[54] SANITARY NAPKIN WITH SELF-CONTAINED DISPOSAL MEANS

[76] Inventor: Steven Mendelsohn, 475 Arizona Ave., Rockville Center, N.Y. 11570

[21] Appl. No.: 271,397

[22] Filed: Nov. 10, 1988

Related U.S. Application Data

[63] Continuation of Ser. No. 80,626, Jul. 31, 1987, abandoned.

[51] Int. Cl.⁴ .............................................. A61F 13/16
[52] U.S. Cl. .................................... 604/387; 604/389
[58] Field of Search ................ 604/386, 387, 389, 390

[56] References Cited

U.S. PATENT DOCUMENTS

| | | | |
|---|---|---|---|
| 3,230,956 | 1/1966 | Kargul | 128/290 |
| 3,274,999 | 9/1966 | Robinson | 128/156 |
| 3,367,334 | 2/1968 | Testa | 128/290 |
| 3,604,423 | 9/1971 | Fraser | 604/385.1 |
| 3,920,019 | 11/1975 | Schaar | 604/385.1 |
| 3,973,567 | 8/1976 | Srinivasan et al. | 128/290 R |
| 4,015,604 | 4/1977 | Csillag | 128/287 |
| 4,020,842 | 5/1977 | Richman et al. | 604/390 |
| 4,023,571 | 5/1977 | Comerford et al. | 128/290 P |
| 4,182,336 | 1/1980 | Black | 128/290 R |
| 4,402,689 | 9/1983 | Baum | 604/387 |
| 4,589,876 | 5/1986 | Van Tilburg | 604/385 R |
| 4,608,047 | 8/1986 | Mattingly | 604/387 |

Primary Examiner—Noah P. Kamen

[57] ABSTRACT

An absorbent pad such as a sanitary napkin having a self-contained disposal means is provided. The napkin is worn in the conventional manner. After use, the self-contained disposal means is folded over the soiled portion of the napkin. The folding over can be accomplished without user contact of the soiled area of the napkin, making the disposal process much less objectionable. Also, as the disposal means completely encloses the soiled napkin, disposal of the napkin can be effected in a sanitary fashion, thus theoretically decreasing the likelihood of transmission of infectious disease.

15 Claims, 2 Drawing Sheets

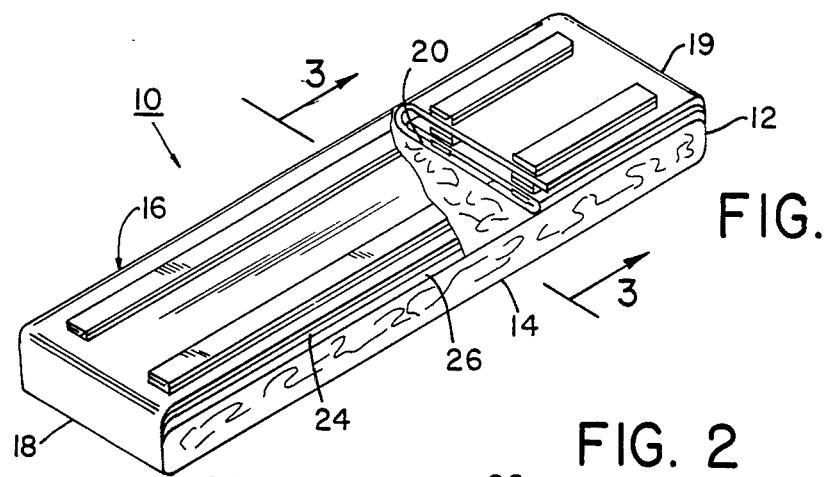
FIG. 1
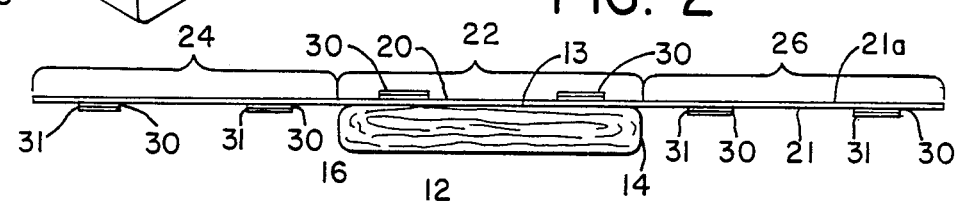
FIG. 2
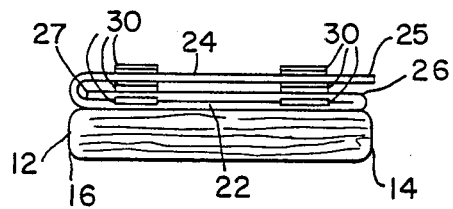
FIG. 3
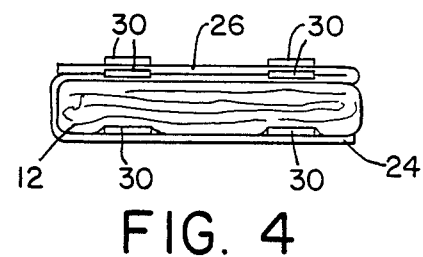
FIG. 4
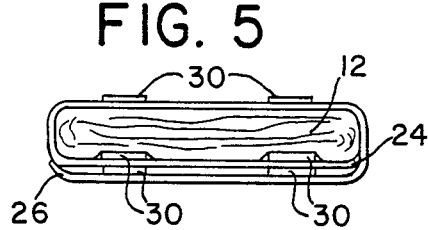
FIG. 5
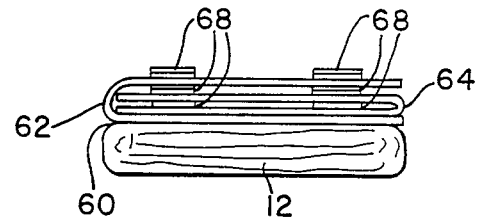
FIG. 6
FIG. 7A
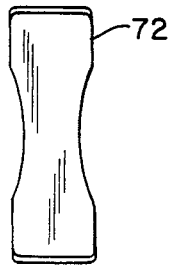
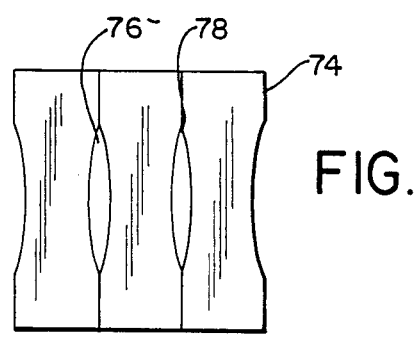
FIG. 7B U.S. Patent  Jul. 11, 1989  Sheet 2 of 2  4,846,828

SANITARY NAPKIN WITH SELF-CONTAINED DISPOSAL MEANS

This application is a continuation of application Ser. No. 80,626, filed July 31, 1987 now abandoned.

BACKGROUND OF THE INVENTION

This invention relates to the packaging, handling and disposing of sanitary napkins, minipads, maxipads, and pantiliners. In particular, it relates to an adhesive attachment system as a means both for protecting a sanitary napkin before use and for disposing of the soiled napkin after use.

Sanitary napkins (for this discussion this term includes minipads, maxipads and pantiliners) are generally attached to a woman's undergarment using strips of adhesive tape or various patterns of adhesive tape affixed to the non-absorptive side of the napkin. The adhesive is so formulated that it is able to attach the napkin securely to the undergarment but allows the napkin to be readily detached after it has been used. In general, this system of securing the napkin during use has been quite successful and convenient for the user.

Much less successful and convenient have been the numerous methods provided for disposing of a soiled napkin. Ideally, a used napkin should be completely sealed in a closed container before disposal. Understandably, there is great reluctance to handle the soiled napkin and frequently it is disposed of in an unwrapped condition, or partially wrapped in multiple layers of toilet tissue, or in a water closet, which often results in the clogging of the waste pipes. Furthermore, incomplete wrapping of a blood-soaked article may in theory result in transmission of infectious diseases such as AIDS.

Various proposals for providing a convenient and sanitary means to dispose of soiled napkins have been suggested. One of these is the provision of small plastic bags with the napkin. One disadvantage of this method is that the user must remember to carry these disposal bags with her. Another disadvantage is that a fair amount of physical manipulation of the used napkin is necessary to place the napkin within the bag. Additionally, these bags have been very flimsy and friable, rendering them very difficult to use.

Another method for disposing of a napkin is shown by A. S. Kargul U.S. Pat. No. 3,230,956 where a pleated plastic covering is affixed to the back side of the napkin. After the napkin has been used, the plastic covering is unfolded and wrapped around the napkin. Some of the disadvantages of this are that it is not believed to be compatible with the adhesive strip method for attachment of the napkin to the undergarment; it is relatively complex to manufacture; and the tear strip, which opens the plastic covering to enable it to be wrapped about the napkin, introduces an opening into the protective sheet which may lead to leakage.

Other methods and disposal systems are suggested in U.S. Pat. Nos. 4,402,689, 3,604,423 and 3,920,019, among many others. In brief, each of these has at least one of the following flaws: it is difficult to use without contacting the soiled napkin; it is prone to leakage in use; and/or it is relatively expensive to make.

Another problem relating to sanitary napkins is protecting the absorptive surface of the napkin prior to use. Usually, a woman carries several napkins in her purse or bag prior to their use. While being carried, they are subject to coming in contact with other items in the purse or bag. These various contacts are clearly undesirable. Although some of the previously mentioned disposal means can be used to protect the napkin prior to the napkin's actual usage, others cannot be so used without disabling them from their primary usage. Those that can be used still suffer from their general awkwardness or complexity.

Thus, there is still a need for a disposal means for a sanitary napkin which can be easily manufactured, is simple to use, and can be used in a way which avoids contact with the soiled section of the napkin, and which will completely and securely seal the napkin. Finally, the same disposal means should be capable of protecting the napkin prior to its use.

OBJECTS OF THE INVENTION

It is an object of this invention to provide a sanitary napkin with a disposal means which solves or alleviates the foregoing problems; one which enables the user to wrap completely the soiled napkin prior to its disposal without contacting its soiled areas.

It is another object of this invention to provide a sanitary napkin with the means of enclosure for disposal incorporated into its basic structure, alleviating the need for carrying an additional separate bag.

It is a further object of this invention to provide a sanitary napkin disposal means which can be readily fabricated at a relatively low cost.

Another object of this invention is to provide a disposal means for a sanitary napkin which can be used in conjunction with adhesive strips for attaching the napkin to the undergarment of the user.

A further object of this invention is to provide a disposal means for a sanitary napkin which can also protect the napkin from soilage prior to its use.

A still further object of this invention is to provide a disposal means for a sanitary napkin which will completely seal the soiled napkin.

Further objects and advantages of the invention will be apparent from the ensuing detailed description of a preferred embodiment thereof, and the novel features will be particularly pointed out in the appended claims.

SUMMARY OF THE INVENTION

In accordance with this invention, a disposal means for a sanitary napkin is provided which is affixed to the non-absorbent surface of the sanitary napkin. This disposal means is fabricated from either one or two sheets of plastic and, when properly manipulated, provides a secure and leakproof wrapping about the sanitary napkin, without the need to touch the soiled napkin, while at the same time being relatively simple to fabricate.

In a preferred embodiment of this invention, a sanitary napkin is provided with a sheet of liquid-impervious material affixed to its back or non-body-contacting side. The sheet is approximately the same length as the sanitary napkin to which it has been attached, but slightly more than three times as wide. During the manufacturing of this disposal means/napkin, the sheet is attached at its entire middle $\frac{1}{3}$ section to the moisture absorbing portion of the napkin. The right $\frac{1}{3}$ section is then folded over the middle section, followed by the left $\frac{1}{3}$ of the sheet being folded over the right section and middle portion. Either a pressure sensitive adhesive is used to seal the short ends of the napkin or the sheet itself is covered with a heat-activated adhesive prior to manufacture. Thus, stamping the ends with either a pressure or heat stamp will seal the ends of the plastic sections. Various adhesive strips are disposed on the right side and left side sections to adhere them to each other and to allow the napkin to be attached to the undergarment.

In the operation of one aspect of the invention, either before storing the napkin in a purse/bag or after using the napkin, the top, left hand flap, which is only unattached on its right facing lengthwise edge, is pulled over the top of the napkin and turned under the bottom, soiled area of the napkin. For the purpose of this description, "top" is defined as the waterproof surface facing the wearer's undergarment and "bottom" is defined as the absorbent surface. The adhesive strips which had attached the flap to the undergarment of the user now adhere to the used side of the napkin. In a similar fashion, the right hand flap, which remains unattached only along its left-facing lengthwise edge, is pulled over the top of the napkin and turned under it to cover the left hand flap. The adhesive strips which had prevented internal slipping now firmly fasten the right and left hand flaps together, completely sealing the napkin without requiring the user to contact the soiled portions of the napkin.

BRIEF DESCRIPTION OF THE DRAWINGS

The following detailed description, given by way of example and not intended to limit the present invention solely to the embodiments shown and described herein, will best be understood in conjunction with the accompanying drawing in which:

FIG. 1 is a perspective view, partially cut-away, of a sanitary napkin with disposal means constructed in accordance with the present invention;

FIG. 2 is a cross-sectional view of the sanitary napkin of FIG. 1, with the disposal means shown during manufacture;

FIG. 3 is a cross-sectional view of the napkin of FIG. 1 at the completion of manufacture;

FIG. 4 shows the napkin of FIG. 1 after the first layer of the wrapper has been involuted;

FIG. 5 shows the invention after the second layer of the wrapper has been involuted and the napkin is ready for disposal;

FIG. 6 is a cross-sectional view of an alternative embodiment of the invention;

FIG. 7A is a perspective view of an alternative embodiment of the invention;

FIG. 7B is a different perspective view of the embodiment of FIG. 7A;

DETAILED DESCRIPTION OF THE EMBODIMENT

Figure 8:
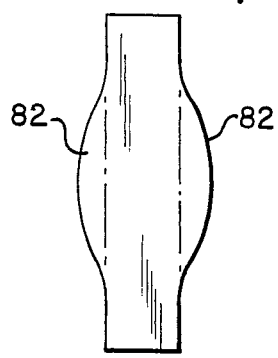
FIG. 8 is a perspective view of another alternative embodiment of the invention.

Although the present invention is specifically directed towards a disposal means for a sanitary napkin, this should not be construed to mean that the invention is limited to sanitary napkins (which term should be read to include pantiliners, minipads, and obstetrical pads) alone. The disposal means described herein is also believed to be useful in making disposable diapers, adult incontinence pads, surgical dressings, wound dressings and other similar products.

FIG. 1 is a perspective view of a sanitary napkin 10 with the disposal means of the present invention incorporated therein. The napkin 10 has a pad 12 which can be made up of many different types of absorptive material such as, for example, comminuted wood pulp fibers, cotton linters, rayon fibers, cotton staple, bleached sulfite creped wadding, and the like. Pad 12 is generally rectangular in form with longitudinal sides 14 and 16, and ends 18 and 19. Although pad 12 is drawn and described in a rectangular form which would be most suitable for use as a sanitary napkin, in other embodiments the shape of pad 12 will be changed to make it useable as an adult incontinence pad, a child's diaper, a surgical dressing or a wound dressing.

During the manufacture of the present invention, an impermeable sheet 20 is glued or otherwise attached to the back or non-body contacting surface 13 of pad 12. This sheet can be made from such materials as polyethylene, polypropylene or cellophane, or other such films. To ease manufacturing, the entire surface 21 of sheet 20 which contacts pad 12 may be coated with a heat-sensitive or pressure sensitive adhesive, such as are well known in the art. The choice of such adhesives will be determined by the ease of its use during the manufacturing process, its known benignity with regards to use in proximity to human skin, and its cost. One example of a suitable adhesive would be styrene. In size the sheet is approximately the same length as pd, but approximately three times greater in width.

Prior to the glueing of the central third of sheet 20 to pad 12, strips 30 of double-sided adhesive tape are applied to the lateral thirds of surface 21 of sheet 20, which is the side that will contact pad 12. Similar strips 30 are applied to the central third of sheet 20, on the surface of sheet 20 which is not glued to pad 12. These strips prevent internal sliding of the plastic layers after construction of the invention has been completed.

Adhesive strips 30 should be permanently bonded to sheet 20. The non-bonded surfaces of the strips should be sufficiently tacky to form a tight seal, but significantly less tacky than that of the bonded surfaces. This is because the contact between the surface of the strips which will be attached to sheet 20 is designed to be permanent. The surface of the strips which does not contact sheet 20 is designed to be tacky, but releasable. Normally, before use, the surface of strips 30 which does not contact sheet 20 will be covered with thin strips of paper 31, plastic or mylar coated on one side, which can be easily removed from strips 30 but which generally protect the strips and prevent them from adhering to anything. This is particularly applicable to the outermost strips which would serve to affix the entire device to the woman's undergarment. In this embodiment, strips 30 may be either narrow or broad and emplaced in three pairs of strips, one pair situated on the right one third of sheet 20, the second pair situated on the left one third of sheet 12 and the third pair situation on the central third of sheet 20 but on the opposite surface of sheet 20 than the surface which is glued to pad 12. In other embodiments different arrangements of the strips are contemplated, as would the use of different sizes of tape.

As seen in FIG. 2, sheet 20 is placed upon pad 12 so that the middle third 22 of the sheet is in contact with the pad, with the adhesive surface of sheet 20 contacting the pad. A pressure stamp or heated stamp, dependent upon whether a pressure-activated or heat-activated adhesive is used, then affixes sheet 20 to pad 12. The right side 26 of sheet 20 is then folded over so that it is even with long edge 16 of pad 12. The left side 24, in a like manner, is folded over so as to be even with the right side edge 14 of pad 12. The sequence of these fold-over operations may be reversed without affecting subsequent manufacturing operations or the use of the napkin. After these fold-over operations, another heat—or pressure—stamping operation occurs. This stamping operation adheres all three layers of sheet 20 together and adheres these layers to pad 12 along the entire width of edges 18 and 19. The strength, and consequently the areas of this stamping must be sufficient so as to prevent any separation of the layers from each other or from the pad during the involuting operations. Although the actual length of each stamped area can vary, it is envisioned that from 1/16" to 3/16" of sheet 20 adjacent to edges 18 and 19 of pad 12 would be adhered to the top of pad 12. Thus, a sandwich of plastic sheets is formed, with the top sheet 24 having only one free edge 25 along its length and the middle sheet 26 also having only one free edge 27 along its length, but with the middle sheet's free edge 27 being opposite to the free edge 25 of the top sheet. This construction and arrangement is shown in FIGS. 1 and 3.

Variations in the form of the pad, such as shown in FIG. 7A, designated as 72, can also be used with the present invention. As shown in FIG. 7B, the hourglass shape of pad 72 requires that sheet 74 be cut in a similar hourglass fashion. In addition to cutting the sheet in a different fashion, an additional stamping operation is required to seal the edges of the arcuate shaped cutouts 76 and 78 to pad 12 and to the folded over layers once they have been folded over the pad of the napkin. The rest of the manufacturing operations and the usage of the napkin remains the same.

Variations can be made for all pad shapes. In FIG. 8 a pad with side flaps 82 presents no obstacle for implementing this invention. The same rectangular configuration for the disposal means could be employed, if the user were provided with instructions to first fold side flaps 82 over the soiled surface of the pad before beginning the involuting process.

An alternative method of construction is shown in FIG. 6. Here, instead of one sheet being used, two separate sheets 62 and 64 are used. Each sheet is approximately the same length as the pad and twice as wide. As in the first embodiment, an adhesive is placed on the surfaces of sheets 62 and 64 which will contact the non-body contacting surface (referred to as the back surface 60) of the pad. Also, a pair of two-sided adhesive strips 68 is placed on the adhesive side of sheets 62 and 64, on the half of the sheets which will not be affixed to the pad. To manufacture the disposal device using two sheets, the two sheets are folded in half. The right half of sheet 62 is laid on top of pad 12 and the left half of sheet 64 is laid on top of the right half of sheet 62. The area of pad 12 which is covered by the right half of sheet 62 and the left half of sheet 64 is then either heat—or pressure—stamped, adhering the sheets to the pad. After this center section has been stamped, the other manufacturing steps are substantially the same as in the first embodiment.

To use the present invention, the thin paper covering strips 31 are removed from the outermost double-sided adhesive strips. This allows the napkin to be attached to the user's undergarments.

If the napkin is to be used as packaged, it would be best not to have paper covering strips 31 on the two inner pairs of double-sided adhesive strips (between 22 and 26 and 26 and 24). These two pairs are designed to prevent intrinsic slipping of the plastic layers against each other which could lead to undesirable displacement or bunching of the napkin.

If the napkin is packaged in an already involuted state for carrying in a purse, it would be necessary to have paper covering strips on all three pairs of double sided adhesive.

After the napkin has been used, it is peeled off from the inner surface of the undergarment. The user then slips her finger between the plastic layers on the back side of the napkin. The adhesive used on the narrow double-sided adhesive strips 30 is so formulated as to be sufficiently tacky to cause the two plastic layers to stick together, but not so strongly adhesive that it cannot be released when desired. Thus, this separation of the plastic layers should not require excess force or be at all difficult.

Once the user has separated the plastic layers, the user grasps the ends of the napkin, which are made of the plastic sheet material and are not soiled in use, and the uppermost plastic layer of the napkin (when viewed looking at the back/non-body contacting side of the napkin) is pulled over the top of the napkin and turned inside out or involuted over the soiled area of the napkin. The adhesive strips which attached the napkin to the undergarment are now against the soiled area of the pad and should grip that area sufficiently well so as to prevent the layer from slipping. This operation is detailed in FIG. 4. At this point, although most of the soiled area of the pad has been covered, including the narrow edges, one long edge of the napkin is still open.

To complete the sealing process, the remaining plastic layer on the back side of the pad is grasped and turned inside out or involuted over the previously involuted sheet. The adhesive strips 30 which hithertofore prevented the sheets from slipping now come in contact with the previously involuted sheet, thereby covering over and sealing the previously mentioned remaining open edge of the napkin as well as fastening the two covering sheets together. At this point the napkin is completely sealed and ready for disposal.

It will be appreciated that the same sequence of steps used to seal the napkin after use could be performed prior to the use of the napkin, provided that the protective paper strips are not removed from the double-sided tapes. When this is done, the pad of the napkin is protected and may be carried in a purse or handbag, ready for use, without picking up incidental contamination. When a napkin needs to be used, one would reverse the sequence of steps used to seal/cover the napkin until the napkin was in its original state. Then the paper strips would be removed, and the normal use sequence begun. It would be possible to alter the manufacture of the disposal means if this "storage" mode becomes the preferred manner in which the napkin is delivered to users. In this case, instead of folding surfaces 24 and 26 over the back surface of paid 12, they could be folded over the front, body-contacting surface of pad 12 during manufacture. Adhesive strips 30 would have to be affixed earlier in the manufacturing process, but all other manufacturing steps would remain the same.

For certain applications, the type of seal commonly known as a "zip-lock" may be incorporated into the invention to obtain the sealed package. The "zip-lock" seal generally consists of two strips of hard plastic material, the one strip being a thin plastic "bar" which is pressed into the other strip. The other strip is comprised of two plastic "bars" with a small space between them. When the first strip is pressed into the space between the two plastic "bars" of the second strip, the first and second strip interlock and a water- and air-tight seal is formed. This type of seal is known in the art, particularly for use in sealing plastic bags. In the context of this invention, the placement of the first and second strips is completely interchangeable.

Figure 9:
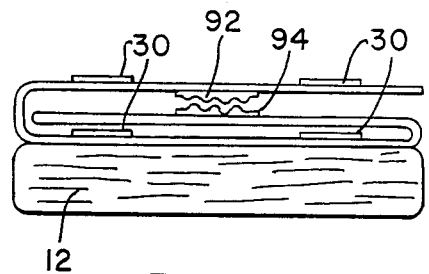
FIG. 9 is a cross-sectional view of yet another alternative embodiment of the invention.

Various embodiments of the present invention can be envisioned which would use "zip-lock" seals. In FIG. 9, one such embodiment is shown. One pair of adhesive strips 30 has been replaced by a "zip-lock seal", comprised of strips 92 and 94. In this embodiment the strips are placed so that they engage each other both before and after involution.

Figure 10:
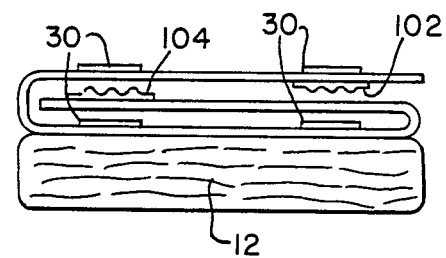
FIG. 10 is a cross-sectional view of still another embodiment of the invention.

FIG. 10 shows an embodiment where a pad is used that is thicker than the one used in FIG. 9. The thicker pad necessitates placing the "zip-lock" strips 102 and 104 at non-opposing locations. The locations are critical only insofar as strips 102 and 104 must mesh with one another after involution.

Figure 11:
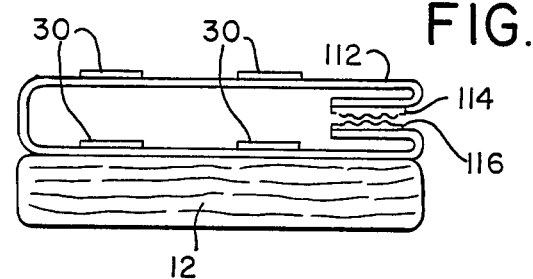
FIG. 11 is a cross-sectional view of another embodiment of the invention.
Figure 12:
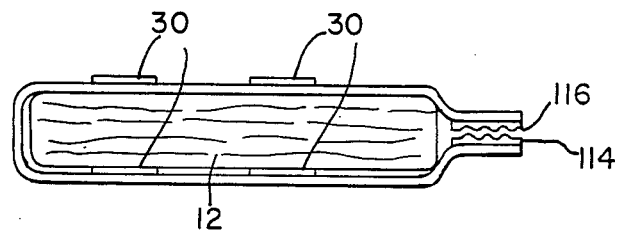
FIG. 12 is a cross-sectional view of the embodiment of FIG. 11 after involution.

For certain napkins and/or surgical dressing configurations, especially very thin and wide ones, a method of construction using a sheet 112 and "zip-lock" seals 114 and 116 may become preferable, both for ease of construction and ease of use. This method of construction is shown in FIG. 11. In this embodiment, sheet 112 is slightly more than twice as wide as the pad of the napkin. Strips 114 and 116, which form the "zip-lock" seal are each attached to the same side and at the opposite edges of sheet 112. As seen in FIG. 11, the sheet is attached to pad 112 with the exact middle of the sheet aligned along one edge of the pad. A pressure- or heating-stamping operation then occurs with the same purpose as the first stamping operation performed to manufacture the preferred embodiment. This operation leaves only the "zip-lock" sealed edges of sheet 112 unattached to the pad. The edges of the sheet upon which the seals have been attached are turned inwards so that they can meet and seal with each other. After use, the seal is opened, the sheet is pulled over the top of the pad and across the soiled surface of the pad. Strips 114 and 116 then meet and are resealed. This construction and operation can be seen in FIG. 12. Adhesive strips 30 are again placed so as to attach the sheet to the user's undergarments and so as to prevent internal slippage.

Many materials other than adhesive strips and "zip-lock" seals may be used for the same purpose. These include but are not limited to pressure-sensitive adhesives, heat—and moisture—sensitive adhesives, and velcro.

While the present invention has been particularly shown and described with reference to preferred embodiments, it will readily be appreciated by those of ordinary skill in the art that various changes and modifications may be made. For example, the double sided adhesive tape placement might be changed to another, equally viable arrangement. Also, the size of the tape strips might vary. Finally, the same disposal means could be implemented with disposable diapers or wound dressings.

It is intended that the appended claims be interpreted as including the foregoing as well a other changes and modifications.

We claim:

1. An absorbent pad having first and second surfaces and provided with a self-contained disposal means, said disposal means comprising:

a substantially impermeable thin sheet foldable into three sections of approximately equal width, the width being substantailly equal to the width of the pad, the length of the sheet being approximately equal to the length of the pad, with one side of the sheet being coated with a thin adhesive film, the second section of the sheet being fixed to the first surface of the pad over their entire common surface area, the remaining unattached first and third sections being folded one atop the other over the second section and affixed to the second section and the pad along only their respective widthwise edges, thereby forming a three layer structure on the first surface of the pad, wherein the first and third sections are capable of being involuted over the second surface of the pad to form a leak resistant disposal means around the pad.

2. The pad of claim 1, wherein the adhesive film is a heat-activated adhesive.

3. The pad of claim 1, wherein the sheet is a thin polyethylene sheet.

4. The pad of claim 1, wherein plural adhesive strips are disposed on at least one of the first and third sections on the same side of the impermeable sheet as is attached to the first surface of the pad.

5. The pad of claim 1, wherein the pad is a sanitary napkin.

6. The pad of claim 1, wherein the pad is an adult incontinence pad.

7. The pad of claim 1, wherein the pad is a disposable diaper.

8. An absorbent pad with a disposal means, the disposal means comprised of:

a substantially impermeable thin sheet having a first, a sheet and a third section, the sections having approximately equal width and length, the width and length of the sections being substantailly equal to the width and length of the pad, the sheet being coated on one side with a thin adhesive film, the second section being attached to the pad over their entire common surface are via said film, and the first and third sections being folded over the second section, one atop the other, and attached to the pad and second section along their width-wise edges.

9. The pad of claim 8, wherein the sheet is a polyethylene sheet.

10. The pad of claim 8, wherein the adhesive is a heat-activated adhesive.

11. The pad of claim 8, wherein plural adhesive strips are disposed on at least one of the first and third sections on the same die of the impermeable sheet as is attached to the first surface of the pad.

12. The pad of claim 8, wherein the pad is a sanitary napkin.

13. The pad of claim 8, wherein the pad is a disposable diaper.

14. The pad of claim 8, wherein the pad is an adult incontinence pad.

15. An absorbent pad with a disposal means, said disposal means comprised of:

a substantially impermeable sheet having first, second and third sections, the sections having equal width and length, and being coated on one side with a thin adhesive film, said sheet being approximately equal in length to the length of said pad, said second section being attached to said pad along its entire surface, and said first and said third sections being folded over said second section and attached to said pad and said second section along their respective width-wise edges, and further wherein adhesive strips are disposed on said third section on the same side of the sheet as is attached to said pad and half of a "zip-lock" seal is disposed on the other side of the third section and the second half of the seal is disposed on the first section, on the same side of the sheet as is attached to the pad.

* * * * *